(12) United States Patent
Felt et al.

(10) Patent No.: US 7,591,853 B2
(45) Date of Patent: Sep. 22, 2009

(54) RAIL-BASED MODULAR DISC NUCLEUS PROSTHESIS

(75) Inventors: Jeffrey C. Felt, Minnetonka, MN (US); Mark A. Rydell, Mntka, MN (US); Stephen H. Crosbie, Mntka, MN (US); John E. Sherman, Wayzata, MN (US)

(73) Assignee: Vertebral Technologies, Inc., Minnetonka, MN (US)

( * ) Notice: Subject to any disclaimer, the term of this patent is extended or adjusted under 35 U.S.C. 154(b) by 0 days.

(21) Appl. No.: 11/372,477

(22) Filed: Mar. 9, 2006

(65) Prior Publication Data
US 2007/0050036 A1    Mar. 1, 2007

Related U.S. Application Data

(60) Provisional application No. 60/685,332, filed on May 24, 2005, provisional application No. 60/700,459, filed on Jul. 19, 2005, provisional application No. 60/660,107, filed on Mar. 9, 2005.

(51) Int. Cl.
*A61F 2/44* (2006.01)
(52) U.S. Cl. ............... 623/17.16; 606/249; 606/252
(58) Field of Classification Search ............ 623/14.12, 623/17.11–17.16, 23.47, 20.14, 20.15, 18.11; 606/61, 63, 249, 252
See application file for complete search history.

(56) References Cited

U.S. PATENT DOCUMENTS

| | | | |
|---|---|---|---|
| 4,772,287 A | 9/1988 | Ray et al. | |
| 4,904,260 A | 2/1990 | Ray et al. | |
| 4,911,718 A | 3/1990 | Lee et al. | |
| 5,192,326 A | 3/1993 | Bao et al. | |
| 5,458,643 A | 10/1995 | Oka et al. | |
| 5,545,229 A * | 8/1996 | Parsons et al. | ........... 623/17.15 |
| 5,609,635 A | 3/1997 | Michelson | |
| 5,702,454 A | 12/1997 | Baumgartner | |
| 5,755,797 A | 5/1998 | Baumgartner | |
| 5,772,661 A | 6/1998 | Michelson | |
| 5,776,199 A | 7/1998 | Michelson | |
| 5,860,973 A | 1/1999 | Michelson | |
| 5,919,236 A | 7/1999 | Pfaff et al. | |
| 6,096,038 A | 8/2000 | Michelson | |
| 6,110,210 A | 8/2000 | Norton et al. | |
| 6,302,914 B1 | 10/2001 | Michelson | |
| 6,387,130 B1 | 5/2002 | Stone et al. | |

(Continued)

OTHER PUBLICATIONS

International Search Report, dated Oct. 30, 2008, pp. 1-3.

(Continued)

*Primary Examiner*—Corrine McDermott
*Assistant Examiner*—Cheryl Miller
(74) *Attorney, Agent, or Firm*—Patterson, Thuente, Skaar & Christensen, P.A.

(57) ABSTRACT

A method and apparatus for repairing a damaged intervertebral disc nucleus in a minimally invasive manner utilizes a modular disc prosthesis preferably comprised of at least three modular segments and at least two rails that operably connect adjacent modular segments. In one embodiment, each modular segment includes a harder inner portion and a softer outer portion. Preferably, the rails operate to slidably connect and interlock adjacent modular segments. A stem portion of the rails that extends outside the periphery of the body of the prosthesis is removable after implantation such that the modular segments form an implanted unitary device that closely mimics the geometry of the disc nucleus cavity.

6 Claims, 9 Drawing Sheets

U.S. PATENT DOCUMENTS

| | | |
|---|---|---|
| 6,443,988 B2 | 9/2002 | Felt et al. |
| 6,468,311 B2 | 10/2002 | Boyd et al. |
| 6,533,818 B1 | 3/2003 | Weber et al. |
| 6,595,998 B2 * | 7/2003 | Johnson et al. ............... 606/90 |
| 6,652,587 B2 * | 11/2003 | Felt et al. ................ 623/20.16 |
| 6,726,721 B2 | 4/2004 | Stoy et al. |
| 6,740,093 B2 | 5/2004 | Hochschuler et al. |
| 6,896,701 B2 | 5/2005 | Boyd et al. |
| 7,001,431 B2 | 2/2006 | Bao et al. |
| 7,008,452 B2 * | 3/2006 | Hawkins .................. 623/17.11 |
| 2002/0026244 A1 | 2/2002 | Trieu |
| 2003/0055506 A1 | 3/2003 | Stoy et al. |
| 2004/0054413 A1 | 3/2004 | Higham et al. |
| 2004/0186576 A1 | 9/2004 | Biscup et al. |
| 2004/0220672 A1 * | 11/2004 | Shadduck ................ 623/17.16 |
| 2005/0010290 A1 * | 1/2005 | Hawkins .................. 623/17.11 |
| 2005/0015150 A1 | 1/2005 | Lee |
| 2005/0055097 A1 | 3/2005 | Grunberg et al. |
| 2005/0154465 A1 | 7/2005 | Hodges et al. |
| 2005/0203599 A1 * | 9/2005 | Garabedian et al. ......... 607/116 |
| 2005/0273178 A1 * | 12/2005 | Boyan et al. ............. 623/23.74 |
| 2006/0106462 A1 | 5/2006 | Tsou |
| 2006/0167550 A1 * | 7/2006 | Snell et al. ................ 623/17.13 |
| 2006/0189999 A1 | 8/2006 | Zwirkoski |
| 2006/0195191 A1 * | 8/2006 | Sweeney et al. .......... 623/17.13 |
| 2006/0247778 A1 * | 11/2006 | Ferree et al. ............. 623/17.14 |
| 2006/0259144 A1 * | 11/2006 | Trieu ....................... 623/17.13 |
| 2006/0293756 A1 | 12/2006 | Felt |
| 2007/0027546 A1 | 2/2007 | Palm |
| 2007/0032874 A1 * | 2/2007 | Lee et al. ................. 623/17.13 |
| 2007/0244485 A1 | 10/2007 | Greenhalgh et al. |
| 2008/0065220 A1 * | 3/2008 | Alleyne et al. ........... 623/17.16 |
| 2008/0119853 A1 | 5/2008 | Felt et al. |
| 2008/0133017 A1 * | 6/2008 | Beyar et al. .............. 623/17.16 |
| 2008/0140206 A1 | 6/2008 | Felt |
| 2008/0208343 A1 | 8/2008 | Felt |

OTHER PUBLICATIONS

International Search Report, dated Sep. 12, 2008, pp. 1-2.

* cited by examiner

RAIL-BASED MODULAR DISC NUCLEUS PROSTHESIS

RELATED APPLICATIONS

The present invention claims priority to U.S. Provisional Patent Application No. 60/685,332, entitled "SPINE DISC NUCLEUS II," filed May 24, 2005, U.S. Provisional Patent Application No. 60/700,459, entitled "SPINE POLYMER PATENT," filed Jul. 19, 2005, and U.S. Provisional Patent Application No. 60/660,107, entitled "MODULAR DISC PROSTHESIS," filed Mar. 9, 2005, the disclosures of which are hereby incorporated by reference. The present invention is also related to U.S. patent application Ser. No. 11/372,357, filed concurrently herewith and entitled, "INTERLOCKED MODULAR DISC NUCLEUS PROSTHESIS", now U.S. Pat. No. 7,267,690, the disclosure of which is hereby incorporated by reference.

FIELD OF THE INVENTION

The present invention relates generally to an implantable prosthesis for repairing damaged intervertebral discs. More particularly, the present invention relates to a rail-based modular disc nucleus prosthesis of predetermined size and shape.

BACKGROUND OF THE INVENTION

The spinal motion segment consists of a unit of spinal anatomy bounded by two vertebral bodies, including the two vertebral bodies, the interposed intervertebral disc, as well as the attached ligaments, muscles, and the facet joints. The disc consists of the end plates at the top and bottom of the vertebral bones, the soft inner core, called the nucleus and the annulus fibrosus running circumferentially around the nucleus. In normal discs, the nucleus cushions applied loads, thus protecting the other elements of the spinal motion segment. A normal disc responds to compression forces by bulging outward against the vertebral end plates and the annulus fibrosus. The annulus consists of collagen fibers and a smaller amount of elastic fibers, both of which are effective in resisting tension forces. However, the annulus on its own is not very effective in withstanding compression and shear forces.

As people age the intervertebral discs often degenerate naturally. Degeneration of the intervertebral discs may also occur in people as a result of degenerative disc disease. Degenerative disc disease of the spine is one of the most common conditions causing pain and disability in our population. When a disc degenerates, the nucleus dehydrates. When a nucleus dehydrates, its ability to act as a cushion is reduced. Because the dehydrated nucleus is no longer able to bear loads, the loads are transferred to the annulus and to the facet joints. The annulus and facet joints are not capable of withstanding their increased share of the applied compression and torsional loads, and as such, they gradually deteriorate. As the annulus and facet joints deteriorate, many other effects ensue, including the narrowing of the interspace, bony spur formation, fragmentation of the annulus, fracture and deterioration of the cartilaginous end plates, and deterioration of the cartilage of the facet joints. The annulus and facet joints lose their structural stability and subtle but pathologic motions occur between the spinal bones.

As the annulus loses stability it tends to bulge outward and may develop a tear allowing nucleus material to extrude. Breakdown products of the disc, including macroscopic debris, microscopic particles, and noxious biochemical substances build up. The particles and debris may produce sciatica and the noxious biochemical substances can irritate sensitive nerve endings in and around the disc and produce low back pain. Affected individuals experience muscle spasms, reduced flexibility of the low back, and pain when ordinary movements of the trunk are attempted.

Degeneration of a disc is irreversible. In some cases, the body will eventually stiffen the joints of the motion segment, effectively re-stabilizing the discs. Even in the cases where re-stabilization occurs, the process can take many years and patients often continue to experience disabling pain. Extended painful episodes of longer than three months often leads patients to seek a surgical solution for their pain.

Several methods have been devised to attempt to stabilize the spinal motion segment. Some of these methods include: heating the annular region to destroy nerve endings and strengthen the annulus; applying rigid or semi-rigid support members on the sides of the motion segment or within the disc space; removing and replacing the entire disc with a generally rigid plastic, articulating artificial device; removing and replacing the nucleus; and spinal fusion involving permanently fusing the vertebrae adjacent the affected disc.

Until recently, spinal fusion has generally been regarded as the most effective surgical treatment to alleviate back pain due to degeneration of a disc. While this treatment is often effective at relieving back pain, all discal motion is lost in the fused spinal motion segment. The loss of motion in the affected spinal segment necessarily limits the overall spinal mobility of the patient. Ultimately, the spinal fusion places greater stress on the discs adjacent the fused segment as these segments attempt to compensate for lack of motion in the fused segment, often leading to early degeneration of these adjacent spinal segments.

Current developments are focusing on treatments that can preserve some or all of the motion of the affected spinal segment. One of these methods to stabilize the spinal motion segment without the disadvantages of spinal fusion is total disc replacement. Total disc replacement is a highly invasive and technically demanding procedure which accesses the disc from an anterior or frontal approach and includes dividing the anterior longitudinal ligament, removing the cartilaginous end plates between the vertebral bone and the disc, large portions of the outer annulus and the complete inner nucleus. Then an artificial total disc replacement is carefully placed in the evacuated disc space. Many of the artificial total disc replacements currently available consist of a generally rigid plastic such as ultra high molecular weight polyethylene ("UHMWPE") as the nucleus that is interposed between two metal plates that are anchored or attached to the vertebral endplates. A summary of the history of early development and designs of artificial discs is set forth in Ray, "The Artificial Disc: Introduction, History and Socioeconomics," Chpt. 21, *Clinical Efficacy and Outcome in the Diagnosis of Low Back Pain*, pgs. 205-225, Raven Press (1992). Examples of these layered total disc replacement devices are shown, for example, in U.S. Pat. Nos. 4,911,718, 5,458,643, 5,545,229 and 6,533,818.

These types of artificial total discs have several disadvantages. First, because the artificial disc replacements are relatively large, they require relatively large surgical exposures to accommodate their insertion. The larger the surgical exposure, the higher the chance of infection, hemorrhage or even morbidity. Also, in order to implant the prosthesis, a large portion of the annulus must be removed. Removing a large portion of the annulus reduces the stability of the motion segment, at least until healing occurs around the artificial disc. Further, because the devices are constructed from rigid materials, they can cause serious damage if they were to displace from the disc space and contact local nerve or vascular tissues. Another disadvantage is that rigid artificial disc replacements do not reproduce natural disc mechanics.

An alternative to total disc replacement is nucleus replacement. Like an artificial disc prosthesis, these nucleus replacements are also inert, non-rigid, non-biological implants. The procedure for implanting a nucleus replacement is less invasive than the procedure for a total disc replacement and generally includes the removal of only the nucleus and replacement of the nucleus with a prosthesis that may be elastically compressible and provide cushioning that mimics a natural disc nucleus. Examples of implants used for nucleus replacement include: U.S. Pat. Nos. 4,772,287, 4,904,260, 5,192,326, 5,919,236 and 6,726,721.

Nucleus replacements are intended to more closely mimic natural disc mechanics. To that end, some nucleus replacements utilize hydrogels because of their water imbibing properties that enable these replacements to expand in situ to permit a more complete filling of the evacuated nucleus cavity. However, there is usually a trade-off in that the more expansion the hydrogel achieves, the less structural support the end product can provide. As a result, many hydrogel nucleus disc replacements have generally adopted the use of some form of a jacket or fabric to constrain the hydrogel material. For example, the implant described in U.S. Pat. Nos. 4,772,287 and 4,904,260 consists of a block of hydrogel encased in a plastic fabric casing. The implant described in U.S. Pat. No. 5,192,326 consists of hydrogel beads enclosed by a fabric shell. Without the jacket or other form of constraint, the hydrogel is susceptible to displacement because of the slippery nature of the hydrogel. Unfortunately, the jacket or fabric shell will be subject to long term abrasive wear issues that could result in failure of the jacket or shell's ability to constrain the hydrogel and thus the hydrogel may be subject to displacement.

Another approach to nucleus replacement involves implantation of a balloon or other container into the nucleus, which is then filled with a biocompatible material that hardens in situ. Examples of this in situ approach to nucleus replacement include U.S. Pat. Nos. 6,443,988 and 7,001,431. One of the problems with this approach is that the chemical hardening process is exothermic and can generate significant amounts of heat that may cause tissue damage. In addition, there is a possibility that the balloon may rupture during expansion, causing leakage of material into the disc cavity and surrounding tissues, which may cause undesirable complications.

Another technique for nucleus replacement involves implanting a multiplicity of individual support members, such as beads, one at a time in the evacuated disc nucleus cavity until the cavity is full. Examples of this approach include U.S. Pat. Nos. 5,702,454 and 5,755,797. Because each of the individual support members or beads is relatively small, there is a possibility that one or more of the individual support members or beads may extrude out of the evacuated disc nucleus cavity. From a mechanical perspective, this technique is limited in the ability to produce consistent and reproducible results because the location and interaction of the multiplicity of beads or support members is not controlled and the beads or support members can shift during and after implantation.

Accordingly, there is a need for a nucleus prosthesis that may be inserted using a minimally invasive procedure and that mimics the characteristics of a natural disc.

SUMMARY OF THE INVENTION

The present invention provides a method and apparatus for repairing a damaged intervertebral disc nucleus in a minimally invasive manner with a modular disc prosthesis. The modular disc prosthesis preferably comprises at least three modular segments and at least two rails that operably connect adjacent modular segments. This configuration allows the prosthesis to be adapted for implantation through various surgical approaches, although the preferred method is the posterolateral ("posterior") approach where the disc is accessed through the patient's back. In one embodiment, each modular segment includes a harder inner portion and a softer outer portion. Preferably, the rails operate with a sliding mechanism to connect and interlock adjacent modular segments. A stem portion of the rails that extends outside the periphery of the body of the prosthesis is removable after implantation such that the modular segments form an implanted unitary device that closely mimics the geometry of the disc nucleus cavity.

In one embodiment, a modular disc prosthesis that is adapted to be implanted in an evacuated disc nucleus cavity includes at least three modular segments each having a width. The first modular segment has a first rail extending at least partially along one side of the width and beyond a periphery of the first modular segment. The second modular segment is slidably connected to the first rail on one side of the width and has a second rail extending at least partially along another side of the width and beyond a periphery of the second modular segment. The third modular segment is slidably connected to the second rail on one side of the width. The prosthesis has an expanded position in which the modular segments are extended along the first and second rails and positioned in a generally end to end configuration spaced apart by the rails prior to implantation. The prosthesis also has an implanted position in which the modular segments are positioned in a generally side by side configuration that defines a unitary body having a generally continuous periphery that generally corresponds to the evacuated disc nucleus cavity with at least a portion of the rails extending beyond the periphery of the body.

Preferably, each modular segment comprises an inner portion and an outer portion. The inner portion includes structure that mates with one of the rails. The outer portion substantially surrounds the inner portion, except for the side having one of the rails and the side having structure that mates with one of the rails. In one embodiment, the inner portion of each modular segment and the outer portion of each modular segment are made of polymers of different durometers. Preferably, the inner portion of each modular segment has a compressive modulus from about 70-100 MPa and the outer portion of each modular segment has a compressive modulus from about 6-20 MPa. The use of a harder inner portion and softer outer portion as part of an integrated unitary implanted device permits the modular prosthesis of the present invention to more closely mimic the stress response of a biological disc nucleus while simultaneously permitting effective operation of the slidable relationship between adjacent modular segments.

In one embodiment, locking features are provided to ensure that the modular disc prosthesis is a unitary device both before and after insertion. To prevent the device from being separated prior to insertion, locking features may be provided on the rigid rails to prevent modular segments from being slid back off of the rails. This ensures that each modular segment is connected in its proper position and in the proper order. In addition, locking features may be provided on the modular segments to lock them together upon insertion. This prevents individual segments from dislocating from the assembled prosthesis and migrating outside of the annulus.

Another aspect of the present invention comprises a method for implanting a modular disc prosthesis. Because the modular disc prosthesis may be implanted one segment at a time, a hole made in the annulus for implantation of the prosthesis may be a fraction of the size of the device in its final assembled form. The first modular segment is inserted into the disc nucleus space through the small hole in the annulus. The second modular segment is then slid up the first rigid rail and into the disc nucleus space until the second modular segment interlocks with the first modular segment. The tail stem of the first rigid rail is then severed from the device. Subsequent modular segments are slid up the adjoining rigid rail into the disc nucleus space and then interlocked with the previously inserted modular segment in a similar manner. Once all of the modular segments have been inserted and all of the tail stems severed, the modular disc prosthesis is fully inserted into the patient's disc nucleus space.

Another aspect of the present invention provides an insertion tool that may be used to aid in the insertion, positioning, and rail removal of the modular prosthesis. The proximal end of the tool has a handle with an enclosed ratchet or roller mechanism attached to and in line with the inner lumen of an elongated tube at the distal end of the tool through which a rail may be inserted. The elongated tube may have a slit or other openings along the length of the tube to aid in threading the rails into the tube. Insertion tool may be provided with a cutting mechanism for removing the rails from the modular segments once they are fully inserted.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE DRAWINGS

Figure 1:
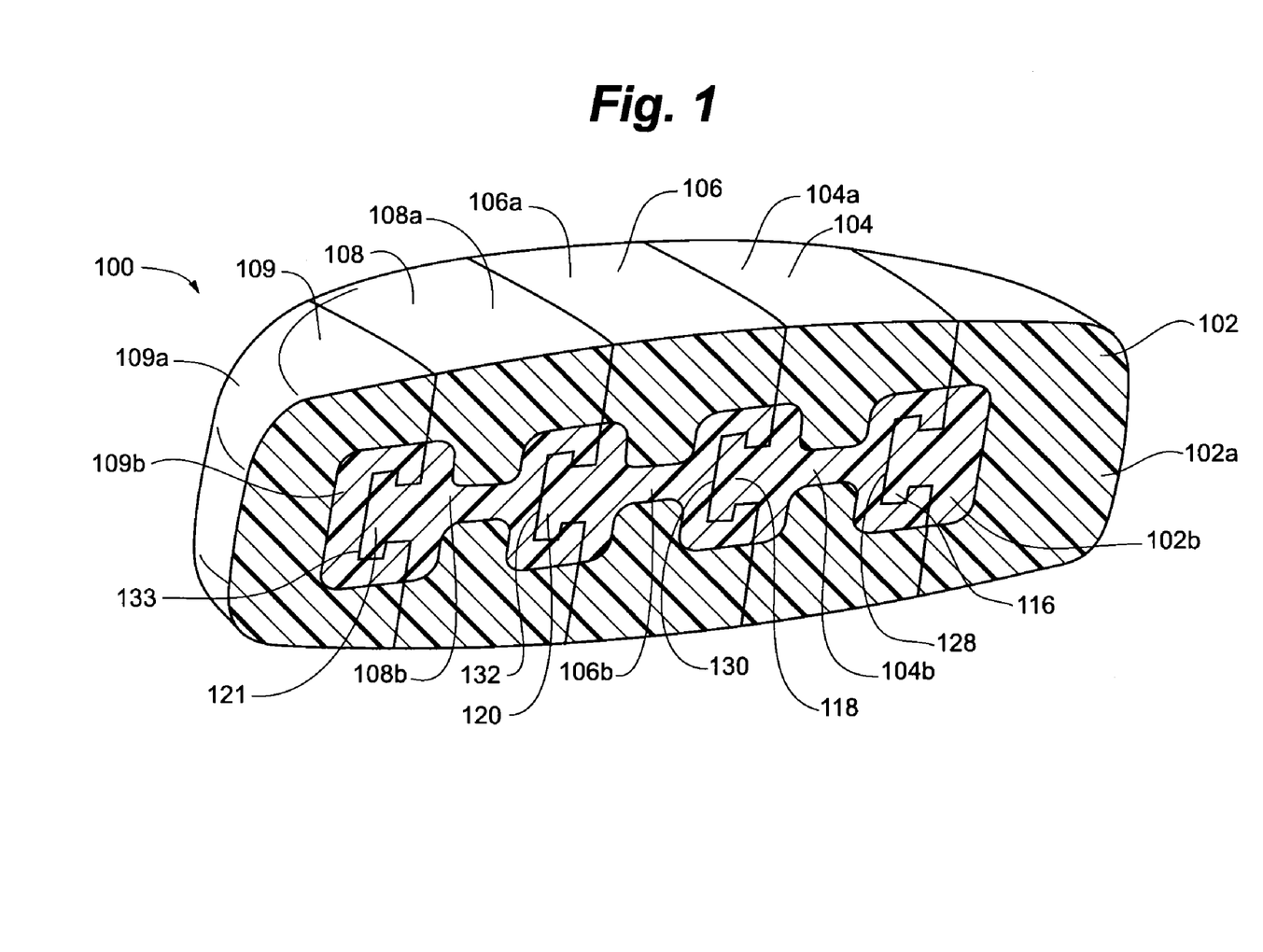
FIG. 1 is a cross-sectional view of a modular disc prosthesis according to the preferred embodiment of the present invention in its inserted configuration.

Referring to FIG. 1, there can be seen a cross-sectional view of a modular disc prosthesis 100 according to the preferred embodiment of the present invention as configured once inserted into the body. In this embodiment, modular disc prosthesis 100 comprises first 102, second 104, third 106, fourth 108, and fifth 109 modular segments. Preferably, each modular segment 102, 104, 106, 108, 109 comprises a soft outer portion 102a, 104a, 106a, 108a, 109a and a hard inner portion 102b, 104b, 106b, 108b, 109b.

In a preferred embodiment, hard inner portions 104b, 106b and 108b have an I-beam cross-sectional shape that optimizes flexibility and strength of the hard inner portions. Alternatively, hard inner portions 104b, 106b, 108b, can have a uniformly shaped cross-sectional area to reduce any differences in compressibility of the modular disc prosthesis 100 across the surface area in order to minimize the potential for stress risers to be created in the interface between the outer surface of the modular disc prosthesis 100 and the inner surfaces of the disc space cavity. It will be recognized that various cross-sectional shapes of hard inner portions 102b, 104b, 106b, 108b and 109b can be utilized in accordance with the present invention and that the cross-sectional shapes of the hard inner portions do not need to be symmetric.

Hard inner portion 102b of first modular segment 102 includes first segment interlocking portion 116. Hard inner portion 104b of second modular segment 104 includes second segment interlocking portion 118 and a first slot 128. Hard inner portion 106b of third modular segment 106 includes third segment interlocking portion 120 and a second slot 130. Hard inner portion 108b of fourth modular segment 108 includes fourth segment interlocking portion 121 and a third slot 132. Hard inner portion 109b of fifth modular segment 109 includes a fourth slot 133.

Figure 9A:
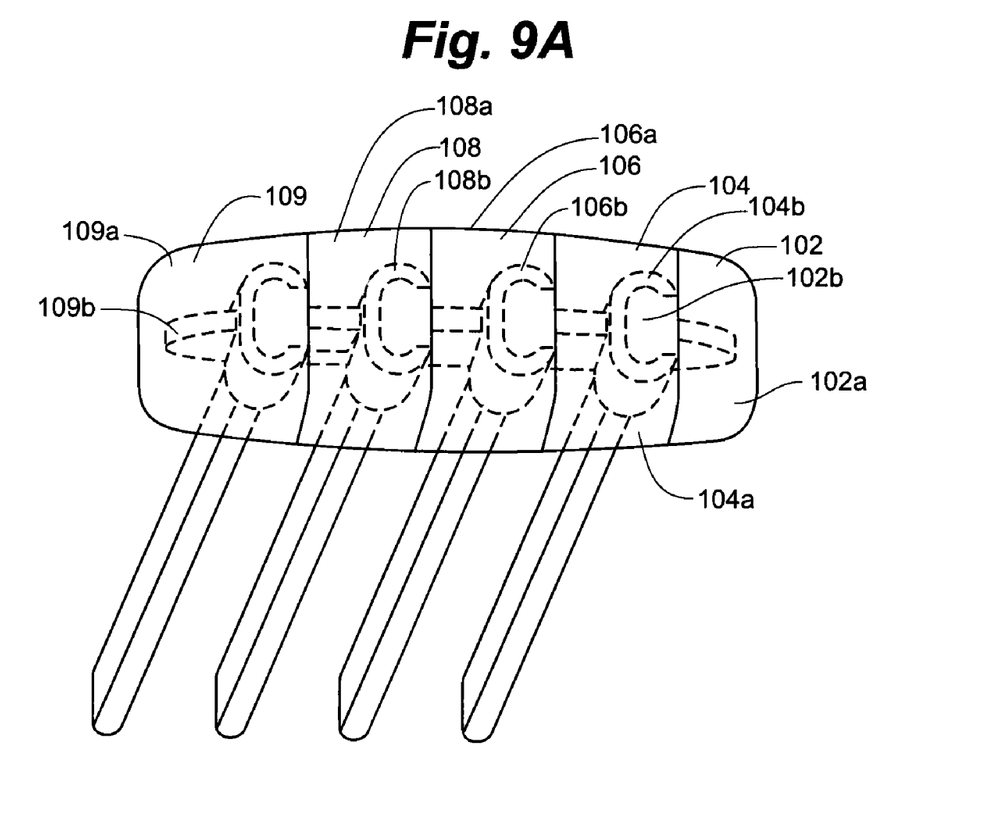
FIG. 9A is a perspective view of a modular disc prosthesis according to the preferred embodiment of the present invention.
Figure 9B:
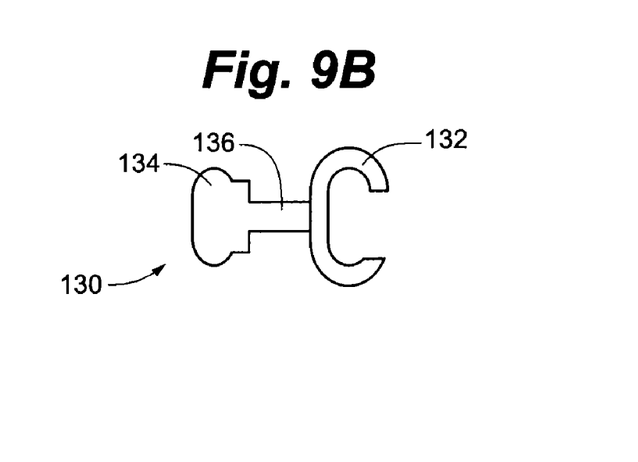
FIG. 9B is a view of an inner portion of a modular segment of a modular disc prosthesis according to the preferred embodiment of the present invention.

In the preferred embodiment, as shown in FIGS. 9A and 9B, the inner portions 102b, 104b, 106b, 108b, and 109b can all be created from the same mold. Note that in FIG. 9A, the outer portions 102a, 104a, 106a, 108a, 109a for modular segments are shown transparent for ease of explanation. As can be seen in FIG. 9A, the hard inner portions of the second 104, third 106, and fourth 108 modular segments are created from a uniform piece 130, the shape of which is more clearly depicted in FIG. 9B. The inner portions for the first 102b and fifth 109b modular segments can each be easily created by grinding down a uniform inner portion 130 as depicted in FIG. 9B. Inner portion 102b of first modular segment 102 is created by grinding off the slot portion 132 of the uniform inner portion 130 and leaving the interlocking portion 134 and a connector portion 136. Inner portion 109b of fifth modular segment 109 is created by grinding off the interlocking portion 134 and retaining the slot portion 132 and the connector portion 136. This ability to form all of the hard inner portions from a single mold allows for quicker, simpler, and less expensive manufacturing.

Figure 2:
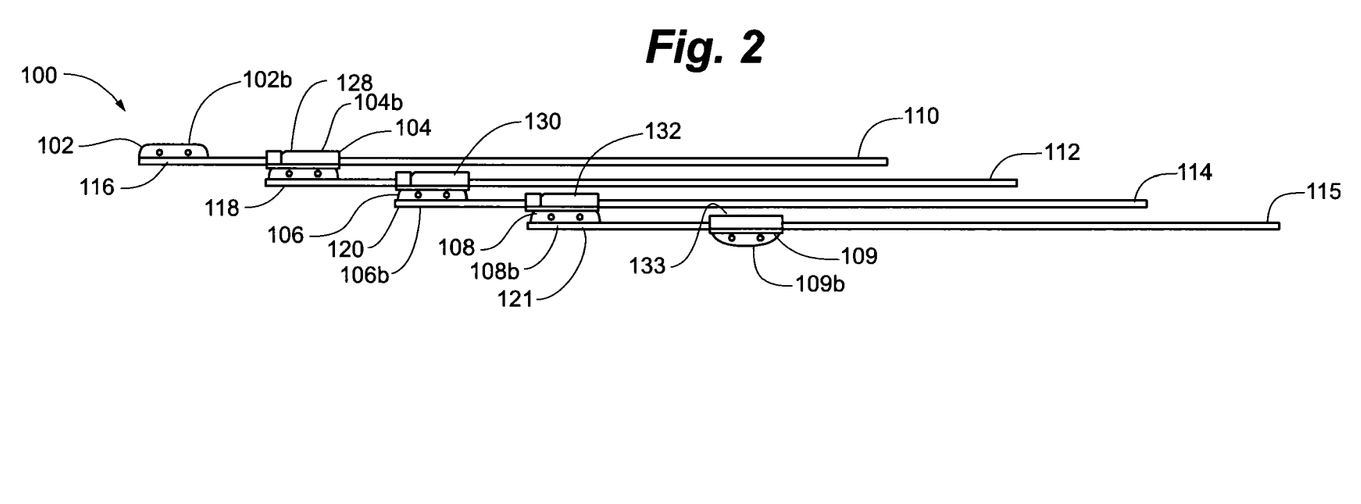
FIG. 2 is a top view of a modular disc prosthesis according to the preferred embodiment of the present invention prior to insertion.

In the preferred embodiment, as shown in FIG. 2, rails 110, 112, 114, 115 have a noncircular cross-sectional shape, although it will be understood that other cross-sectional shapes could be utilized and that there is no requirement that all of the rails have similar cross-sectional shapes. It has been found that the noncircular cross-sectional shape as shown (corresponding mating C and sideways T cross-sectional shapes) provides for better alignment of the modular segments and supports larger insertion forces along the axis of the rail.

It will be understood that in the preferred embodiment, the rails 110, 112, 114, 115 of the present invention have a non-uniform cross-sectional aspect ratio in terms of the height and width of the rail. Preferably, the rails have a relative rigidity along a longitudinal axis of the rail in a dimension of the height of the rail that is greater than a width of the rail, whereas in a dimension transverse to the width of the rail the relative rigidity of the rail permits a greater degree of flexibility such that succeeding modular segments can be moved laterally with respect to one another in the expanded position without deforming the rails. Preferably, the height of the rail is in the range of about 1 mm to 6 mm and the width of the rail is in the range of about 0.5 mm to 4 mm. This differential rigidity in the two dimensions transverse to the longitudinal axis of the rail is important in permitting effective and efficient sliding operation of the adjacent modular segments.

Referring to FIG. 2, there can be seen a portion of a modular disc prosthesis 100 according to the preferred embodiment of the present invention prior to insertion into the evacuated disc nucleus cavity. Note that in FIG. 2, modular disc prosthesis 100 is depicted showing only the hard inner portion 102b, 104b, 106b, 108b, 109b of each modular segment 102, 104, 106, 108, 109 for convenience of illustration. However, in the preferred embodiment of the invention each modular segment would also have a soft outer portion as described above and shown in FIG. 1.

In alternate embodiments, the modular disc prosthesis may comprise greater or fewer numbers of modular segments and rails, as long as there are at least three modular segments and two rails. For example, FIG. 3 depicts a modular disc prosthesis 200 having four modular segments and three rails.

Prior to insertion, modular disc prosthesis 100 further includes first 110, second 112, third 114, and fourth 115 rails. First modular segment 102 is rigidly attached to first rail 110 at first segment interlocking portion 116. Second modular segment 104 is slidably attached to first rail 110 at first slot 128 and rigidly attached to second rail 112 at second segment interlocking portion 118. Third modular segment 106 is slidably attached to second rail 112 at second slot 130 and rigidly attached to third rail 114 at third segment interlocking portion 120. Fourth modular segment 108 is slidably attached to third rail 114 at third slot 132 and rigidly attached to fourth rail 115 at fourth segment interlocking portion 121. Fifth modular segment 109 is slidably attached to fourth rail 115 at fourth slot 133.

Figure 3:
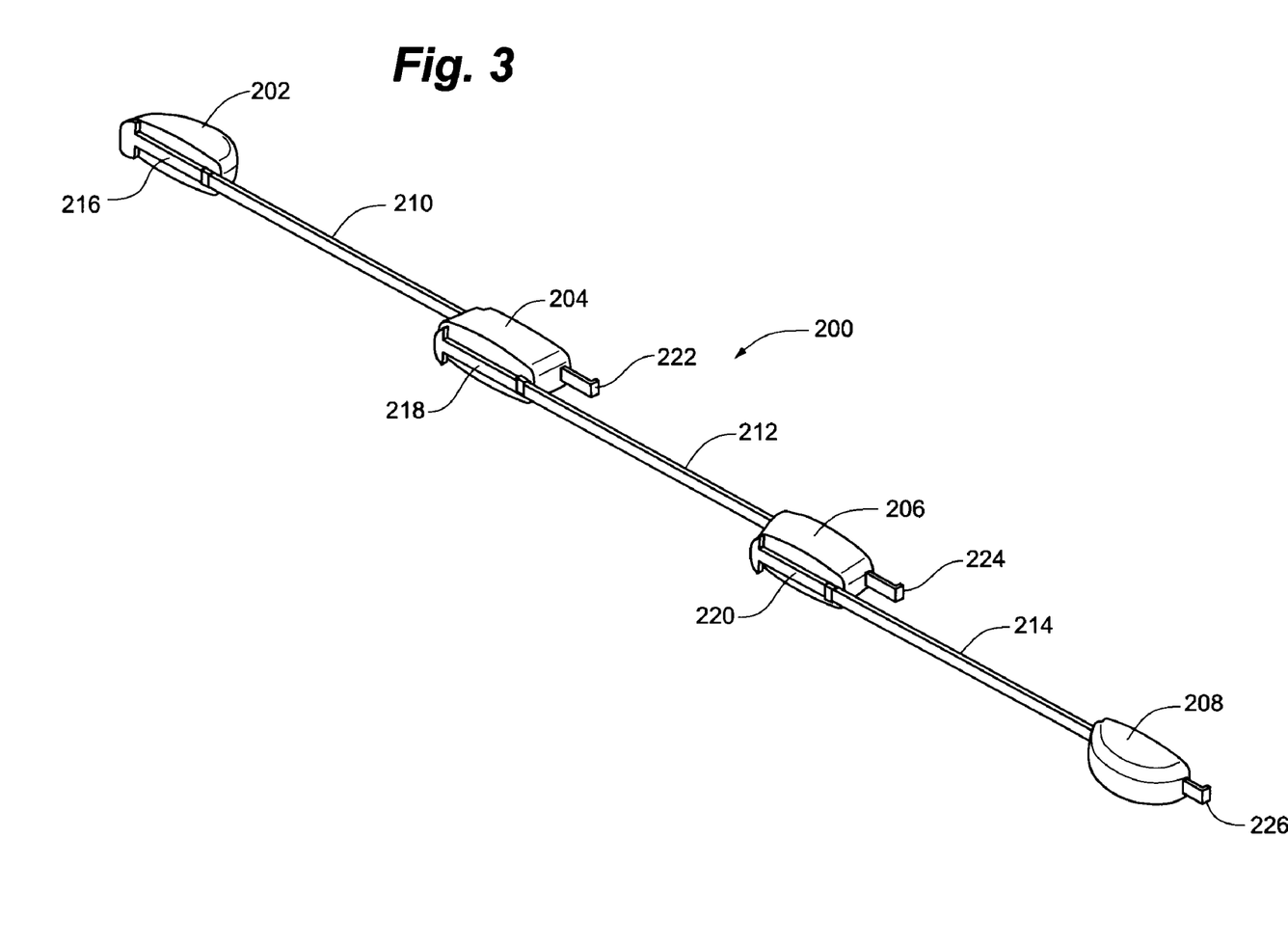
FIG. 3 is a perspective view of a modular disc prosthesis according to an alternate embodiment of the present invention prior to insertion.

As shown in FIG. 2 and FIG. 3, each rail 110, 112, 114 and 115 or 210, 212 and 214 includes a stem portion that extends beyond a periphery of the body of the prosthesis 100, 200, respectively. Preferably these stem portions are long enough to permit access into the evacuated disc nucleus space such that one modular segment can be positioned inside the evacuated disc nucleus cavity while the next modular segment on the rail is still outside of the body. In an exemplary embodiment, the length of the stem portions ranges between 6 cm-20 cm.

As shown in the alternate embodiment of FIG. 3, each rail 210, 212, 214 may further include a retaining portion 222, 224, 226 to keep the device from being separated prior to insertion. The retaining portions 222, 224 and 226 are configured to prevent the corresponding modular segments 204, 206 and 206 from sliding off the rails. The retaining portions may be molded into the rails or may be separate pieces or deformations of the rails added during the manufacture of the device.

The preferred embodiment is a unitary prosthesis that is packaged, sterile, and ready for implantation at the surgical site. Since the device is fully preformed and delivered as a unitary implant, the device is under direct surgeon control until the disc nucleus prosthesis is completely formed. This unitary design reduces the need for the surgeon to determine how to configure the prosthesis to allow for the most efficacious filling of the evacuated disc nucleus cavity and assures that the components' order of insertion and connection are properly achieved. The ability to predetermine the size of the modular disc prosthesis also allows for the evacuated disc nucleus cavity to be more completely filled and provides a greater degree of control over the uniformity of the stress response of the implant as compared to other kinds of minimally invasive implants. In this regard, it will be understood that the modular disc prosthesis 100 of the present invention may be provided in a variety of different final assembled volumes and shapes to correspond to different sizes and shapes of different evacuated disc nucleus cavities.

Figure 8:
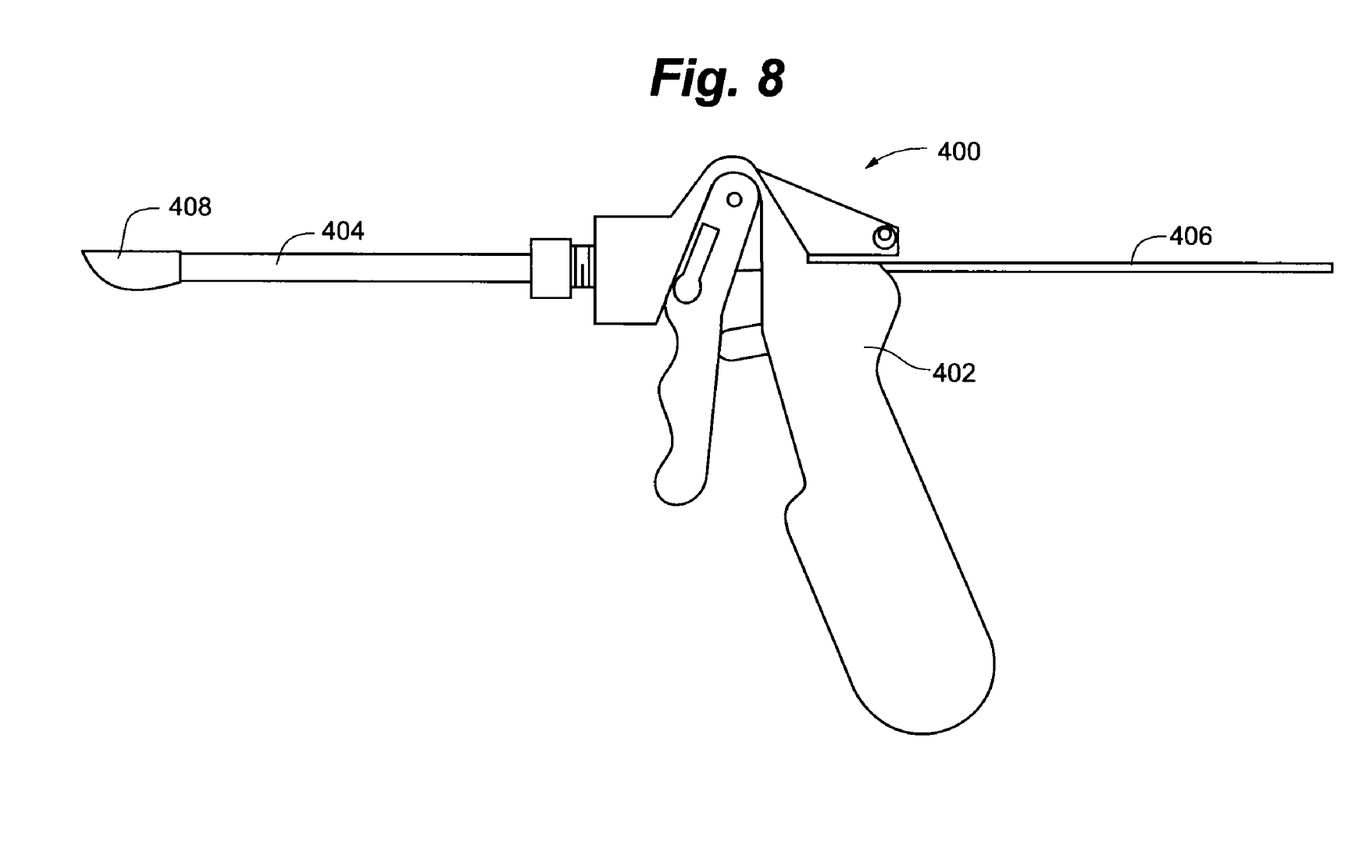
FIG. 8 is a view of an insertion tool for use in accordance with an embodiment of the present invention.

Modular disc prosthesis 100 may be introduced through an access tube that is inserted partially into the disc nucleus space. Access tube is at least 3 inches long and preferably about 6 inches long. An insertion tool 400 as shown in FIG. 8 may be used to aid in the insertion, positioning, and rail removal of the modular prosthesis. The proximal end of the tool 400 has a handle 402 with an enclosed ratchet or roller mechanism attached to and in line with the inner lumen of an elongated tube 404 at the distal end of the tool through which a rail 406 may be inserted. The elongated tube 404 may have a slit or other openings along the length of the tube 404 to aid in threading the rails 406 into the tube. Insertion tool 400 can then be used to guide modular segments 408 into the disc space. The insertion tool 400 may be made out of any combination of plastics, metals, ceramics, or the like.

It should be noted that although the insertion of modular disc prosthesis 100 is described in relation to a preferred five-segment embodiment or an alternate four-segment embodiment, embodiments having any other number of segments would be inserted in a similar fashion.

Figure 4:
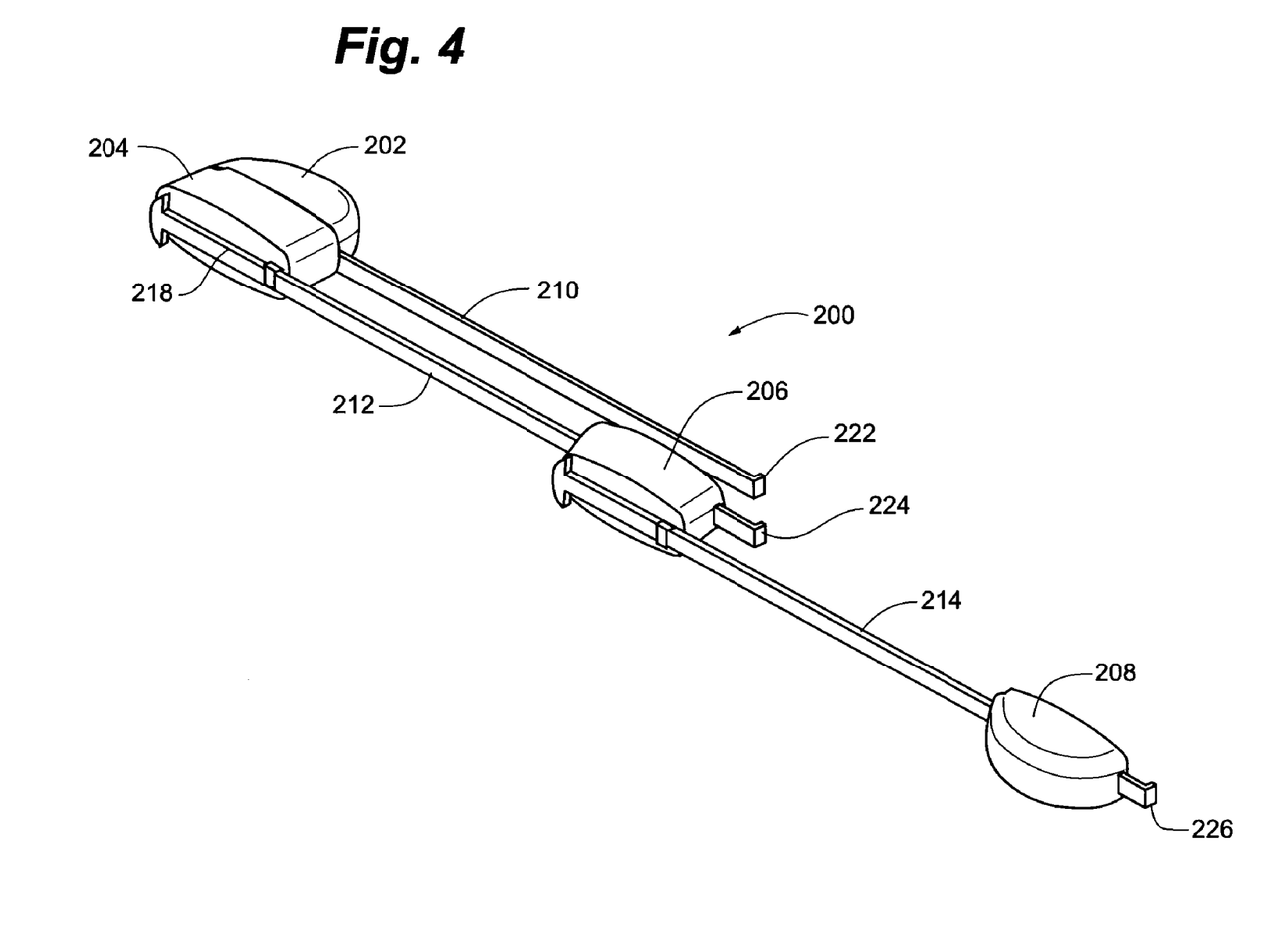
FIG. 4 is a perspective view of a modular disc prosthesis according to an alternate embodiment of the present invention at a first stage of insertion.

Referring again to FIG. 3, there can be seen a modular disc prosthesis 200 prior to insertion into the body. Upon inserting the access tube into the disc nucleus space, the first rail 210 is threaded through the lumen of the elongated tube 404 of the insertion tool 400. The insertion tool 400 is then used to push first modular segment 202 through the tube and into the disc space. Upon complete insertion of first modular segment 202, modular disc prosthesis 200 is moved centrally and the insertion tool 400 is repositioned onto the first rail 210 proximal to second modular segment 204 which is slid along the first rail 210 into the evacuated disc nucleus space onto first segment interlocking portion 216 until it is flush with first modular segment 202. This stage of insertion is depicted in FIG. 4. A stem portion of first rail 210 is then removed and modular disc prosthesis 200 is moved centrally again.

Figure 5:
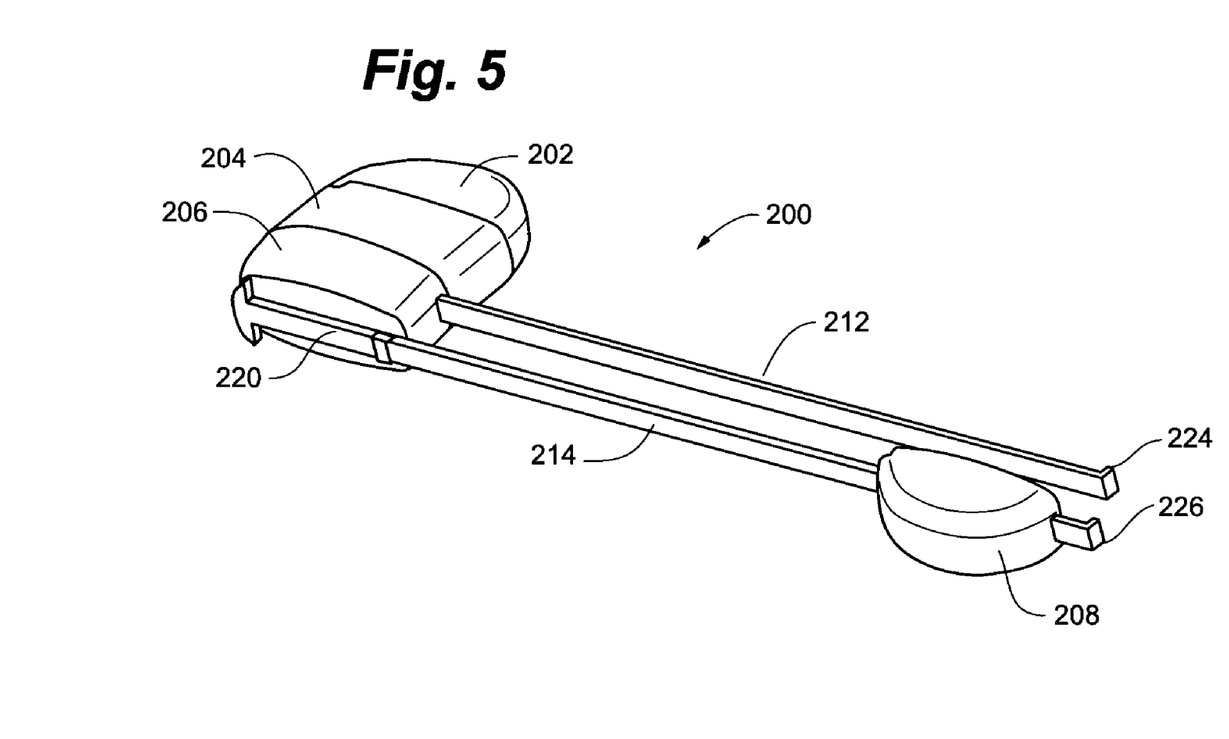
FIG. 5 is a perspective a view of a modular disc prosthesis according to an alternate embodiment of the present invention at a second stage of insertion.
Figure 6:
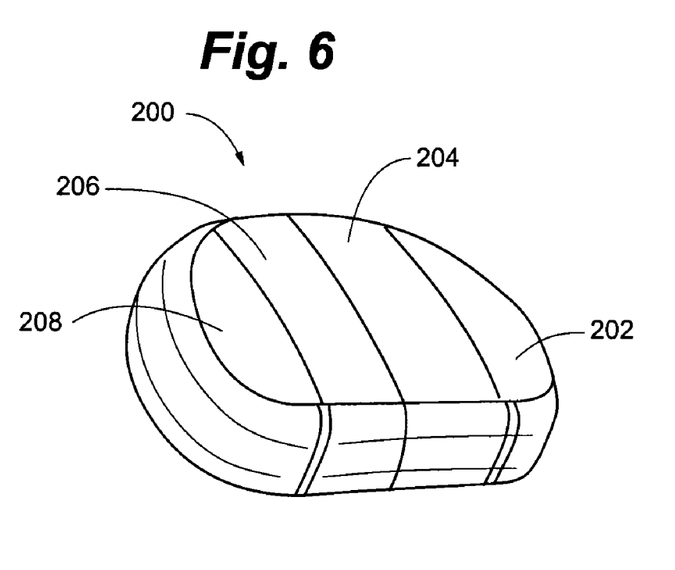
FIG. 6 is a perspective view of a modular disc prosthesis according to an alternate embodiment of the present invention at a final state of insertion.

Second rail 212 is then threaded through insertion tool 400 and third modular segment 206 is slid down second rail 212 and into the disc nucleus space onto second segment interlocking portion 218 until it is flush with second modular segment 204. This configuration is shown in FIG. 5. A stem portion of second rail 212 is then removed and modular disc prosthesis 200 is moved centrally. Third rail 214 is then threaded through insertion tool and fourth modular segment 208 is slid along third rail 214 into the disc nucleus space and onto third segment interlocking portion 220 until it is flush with the other modular segments 202, 204, 206. Finally, a stem portion of third rail 214 is removed. This final implanted configuration of modular disc prosthesis 200 with all modular segments aligned and locked together is shown in FIG. 6. Modular disc prosthesis 200 is sized and shaped to conform to the geometry of the evacuated disc nucleus cavity.

In an alternate embodiment, a keystone approach can be used to insert the modular disc prosthesis such that the last modular segment inserted into the disc nucleus space is not one of the outside segments. Instead, the outside segments can be the first two segments inserted. This creates a bilateral expansion force as the remaining segments are inserted between the two outside segments. This helps make a tighter fit within the evacuated disc nucleus cavity than does the asymmetric lateral force imparted when the segments are implanted sequentially.

The stem portions of rails 110, 112, 114, 115 that extend beyond the periphery of the body of the modular disc prosthesis 100 can be removed by many different techniques. Insertion tool 400 may be provided with a cutting mechanism that can remove the stem portions of the rails. The cutting mechanism may be a pair of fixed blades located on the distal end of the pushing tool. In this embodiment, the cutting blades would act as a cutting wheel in which a turning of the handle connected to the blades causes the blades to circumscribe the rail. Alternatively, the cutting mechanism can be a clamping means that removes the rails through twisting or pinching. Stem rails may also be cut off with any other sharp instrument.

In another embodiment, the stem portions of the rails may be provided with a perforation at the junction with each modular segment such that they can be torn, broken, twisted, or more easily cut off. Cutting may also be accomplished with a wire loop provided to the part. Additionally, heat, laser, or any other local energy source can be used to accomplish the separation. One of skill in the art will recognize that numerous alternative means exist whereby stem rails can be severed from the modular disc prosthesis.

Alternatively, the modular disc prosthesis may be implanted using an anterior lateral approach. An anterior lateral approach allows for a larger insertion opening to be used while still being minimally invasive. In this approach, the disc is accessed from the patient's side through the psoas muscle, which avoids major nerve and vascular tissues, and may be used in the presence of medical conditions mitigating against the posterior approach. This approach is essentially oriented 90° from the posterior approach. In this embodiment, it may be acceptable to have only two modular segments that comprise the prosthesis with the side-by-side orientation of the segments being generally medial-to-lateral instead of posterior-to-anterior.

During insertion, slots 128, 130, 132, 133 slide along the stem portions of rails 110, 112, 114, 115 and onto segment interlocking portions 116, 118, 120, 121. Slots 128, 130, 132, 133 and segment interlocking portions 116, 118, 120, 121 may be provided with locking features to prevent separation of modular segments 102, 104, 106, 108, 109. Locking features, such as a barb or stud or a series of barbs or studs, may be provided such that once a slot is slid onto a segment interlocking portion, it cannot be slid back off of it. A ratchet and pawl may also be used to lock modular segments together. A ratchet release tool may also be provided in case separation of modular segments is desired once they are locked together.

Figure 7:
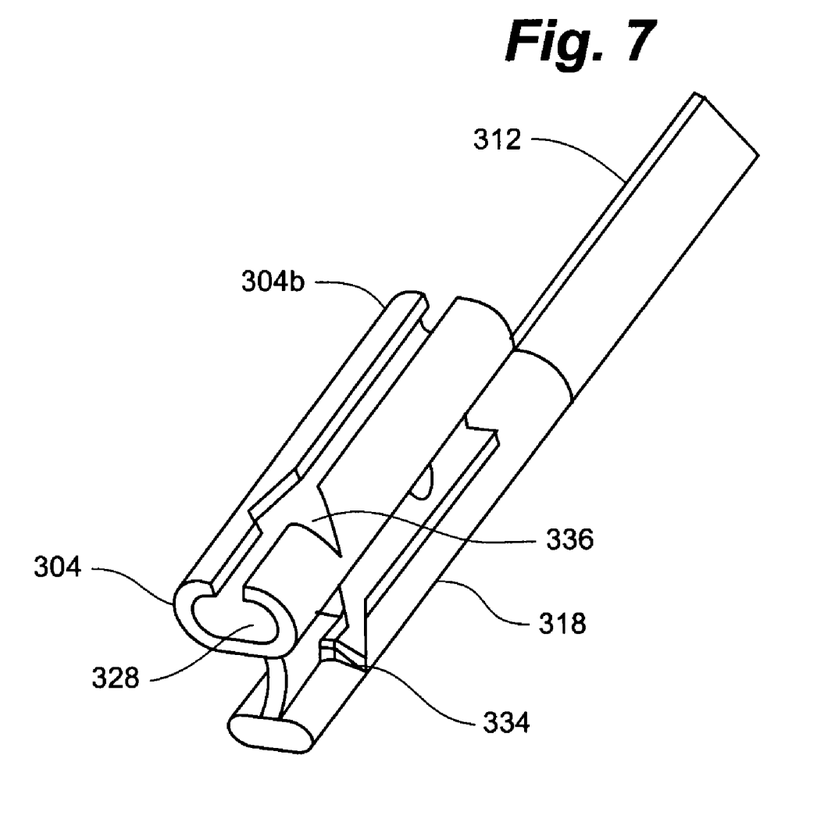
FIG. 7 is a partial perspective view of a portion of a modular disc prosthesis according to an embodiment of the present invention.

One example of these locking features is depicted in FIG. 7. Hard inner portion 304*b* of each modular segment 304 is provided with a pair of depressible projections 334 on segment interlocking portion 318 and a complementary pair of apertures 336 on slot 328. When slot 328 of a first modular segment 304 is slid onto segment interlocking portion 318 of a second modular segment, projections are depressed. When apertures of the first modular segment are positioned over projections of the second modular segment, the projections pop through apertures 336, locking the modular segments relative to one another. Modular segments may be separated by depressing the projections and sliding the first modular segment back off of the second modular segment.

Alternatively, free movement of modular segments 102, 104, 106, 108, 109 along rails 110, 112, 114, 115 may be allowed until insertion in the body. It will be understood that, depending upon the material configuration of the modular prosthesis 100 and the interface fit, segment interlocking portions 116, 118, 120, 121 may swell due to hydration to lock in the final configuration. This feature may be used alone or in combination with a mechanical locking feature. Alternative methods of locking modular segments together will be appreciated by those skilled in the art.

In the preferred embodiment, modular disc prosthesis 100 is molded from elastomeric biomaterials, preferably polyurethane. Stem rails 110, 112, 114, 115 and hard inner portions 102*b*, 104*b*, 106*b*, 108*b*, 109*b* are made from a hard durometer polyurethane, such as a polyurethane with a Shore D hardness of about 45 or above and compressive modulus in the range of about 70 to 100 MPa. Soft outer portions 102*a*, 104*a*, 106*a*, 108*a*, 109*a* are made from a softer durometer polyurethane, such as a polyurethane with a Shore A hardness ranging from about 40 to 80 and a compressive modulus in the range of about 6 to 20 MPa.

In the preferred embodiment, the two different durometer polyurethanes may be co-polymerized to create a chemical bond between the two portions of each modular segment 102, 104, 106, 108, 109. In alternate embodiments, other polymers such as PEEK, polyethylene, silicones, acrylates, nylon, polyacetyls, and other similar biocompatible polymers may be used for the hard inner portions or the soft outer portions.

In an alternate embodiment, the stem of the tails may be molded from a harder durometer material than soft outer portion and hard inner portion of modular segments. Utilizing this approach allows the rails to be extruded, rather than molded as part of the modular segments. A bond joint can then be made with the hard inner portion external to the periphery of the modular segments to form the unitary design. Extruding the stem portions of the tails makes the modular disc prosthesis easier and less expensive to manufacture than a completely molded product.

In the preferred embodiment, the modular disc prosthesis is deformable in response to normal physiological forces of 30 to 300 pounds. Because of this deformability, the prosthesis produces a physiologically appropriate amount of loading on the end plates of the intervertebral disc. As a result, the end plates will not excessively deform over time and ultimately conform to the contours of the implant as is the case with many more rigid disc nucleus replacement implants.

In an alternate embodiment, the outer shell of the modular disc nucleus prosthesis may be modified to provide for elution of medicants. Such medicants may include analgesics, antibiotics, antineoplastics or bioosteologics such as bone growth agents. While motion preservation is generally a principle goal in nucleus replacement, in certain indications it may be desirable to promote some bony fusion. Such indications may include nucleus replacements in the cervical spine.

The solid polymer outer shell of the modular disc nucleus prosthesis may provide for better and more controllable elution rates than some hydrogel materials. In an alternate embodiment, the modular disc nucleus prosthesis may include different elution rates for each polymer material. This would allow for varying elution rates for different medicants.

Various modifications to the disclosed apparatuses and methods may be apparent to one of skill in the art upon reading this disclosure. The above is not contemplated to limit the scope of the present invention, which is limited only by the claims below.

The invention claimed is:

1. A modular disc prosthesis that is adapted to be implanted in an evacuated disc nucleus space, the prosthesis comprising:
   a first modular segment having a width and having a first rail extending at least partially along one side of the width;
   a second modular segment having a width and slidably connected to the first rail on one side of the width and having a second rail extending at least partially along another side of the width;
   a third modular segment having a width and slidably connected to the second rail on one side of the width;
   wherein the prosthesis has an expanded position in which the modular segments are extended along the first and second rails and positioned in a generally end to end configuration spaced apart by the rails prior to implantation and an implanted position in which the modular segments are positioned in a generally side by side configuration;
   wherein each modular segment comprises an inner portion including structure that mates with one of the rails and an outer portion substantially surrounding the inner portion except for the side having one of the rails and the side having structure that mates with one of the rails;
   wherein the inner portion of each modular segment and the outer portion of each modular segment are made of polymers of different durometers, the inner portion of each modular segment having a compressive modulus that is greater than a compressive modulus of the outer portion of each modular segment, the compressive modulus of the outer portion being in the range from about 6-20 MPa; and
   wherein the inner portion of each modular segment has a compressive modulus in the range from about 70 MPa to about 100 MPa.

2. The modular disc prosthesis of claim 1, wherein the polymers of the inner portion and the outer portion of each modular segment are copolymerized.

3. The modular disc prosthesis of claim 1, wherein at least a portion of the polymer of the outer portion further comprises at least one medicant operably carried by the polymer to be eluted after the prosthesis is implanted.

4. A modular disc prosthesis that is adapted to be implanted in an evacuated disc nucleus space, the prosthesis comprising:
   a first modular segment having a width and having a first rail extending at least partially along one side of the width;
   a second modular segment having a width and slidably connected to the first rail on one side of the width and having a second rail extending at least partially along another side of the width;
   a third modular segment having a width and slidably connected to the second rail on one side of the width;
   wherein the prosthesis has an expanded position in which the modular segments are extended along the first and second rails and positioned in a generally end to end configuration spaced apart by the rails prior to implantation and an implanted position in which the modular segments are positioned in a generally side by side configuration;
   wherein each modular segment comprises an inner portion including structure that mates with one of the rails and an outer portion substantially surrounding the inner portion except for the side having one of the rails and the side having structure that mates with one of the rails;
   wherein the inner portion of each modular segment and the outer portion of each modular segment are made of polymers of different hardness, the inner portion of each modular segment having a hardness that is greater than a hardness of the outer portion of each modular segment; and
   wherein the outer portion of each modular segment has a Shore A hardness ranging from about 40 to 80 and the inner portion of each modular segment has a Shore D hardness of about 45 or above.

5. The modular disc prosthesis of claim 4, wherein the polymers of the inner portion and the outer portion of each modular segment are copolymerized.

6. The modular disc prosthesis of claim 4, wherein at least a portion of the polymer of the outer portion further comprises at least one medicant operably carried by the polymer to be eluted after the prosthesis is implanted.

* * * * *